United States Patent
Hassan et al.

(10) Patent No.: US 12,325,651 B2
(45) Date of Patent: Jun. 10, 2025

(54) BIODESALINATION USING MICROBIAL ATTACHED GROWTH CULTIVATION

(71) Applicant: United Arab Emirates University, Al-Ain (AE)

(72) Inventors: Ashraf Aly Hassan, Al-Ain (AE); Abdul Mannan Zafar, Al-Ain (AE); Endalkachew Sahle-Demessie, Cincinnati, OH (US)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 18/100,227

(22) Filed: Jan. 23, 2023

(65) Prior Publication Data
US 2024/0246844 A1 Jul. 25, 2024

(51) Int. Cl.
*C02F 3/34* (2023.01)
*C12N 1/12* (2006.01)
*C02F 101/12* (2006.01)
*C02F 103/08* (2006.01)

(52) U.S. Cl.
CPC ........... *C02F 3/348* (2013.01); *C12N 1/12* (2013.01); *C02F 2101/12* (2013.01); *C02F 2103/08* (2013.01); *C02F 2305/06* (2013.01)

(58) Field of Classification Search
None
See application file for complete search history.

(56) References Cited

U.S. PATENT DOCUMENTS

| | | | | |
|---|---|---|---|---|
| 4,937,210 A | * | 6/1990 | Jones | C04B 38/0051 502/80 |
| 5,910,245 A | * | 6/1999 | Bernhardt | B09C 1/10 210/170.07 |
| 6,423,229 B1 | * | 7/2002 | Mao | C02F 3/2806 210/603 |
| 2004/0062687 A1 | * | 4/2004 | Dordick | B01J 19/0046 422/400 |
| 2014/0142353 A1 | * | 5/2014 | Hitzl | C10G 1/008 422/111 |

(Continued)

OTHER PUBLICATIONS

Dayana Arias et al., Partial desalination of seawater for mining processes through a fluidized bed bioreactor filled with immobilized cells of Bacillus subtilis LN8B, Desalination, vol. 482, 2020,114388, ISSN 0011-9164 (Year: 2020).*

(Continued)

*Primary Examiner* — Chester T Barry
(74) *Attorney, Agent, or Firm* — Hayes Soloway P.C.

(57) ABSTRACT

A biological desalination process to remove salt from seawater using naturally grown algae or cyanobacteria in an attached growth photobioreactor setup. The photobioreactor (PBR) structure can be vertical or horizontal in orientation. Any shape of PBR can provide more light contact to the algae or cyanobacteria for enhanced growth on support media. The reactor can be designed in a way that can get maximum exposure to sunlight. The influent seawater is mixed with nutrients that are essential for the growth of algae or cyanobacteria. The main objective is to remove the salt from the brackish, saline, hypersaline or seawater. The influent seawater can be treated using the attached growth of algae or cyanobacteria, and the effluent from the PBR can be further treated based on desired water use.

18 Claims, 8 Drawing Sheets

(56) References Cited

U.S. PATENT DOCUMENTS

| 2015/0353379 | A1* | 12/2015 | Lee | C02F 1/043 |
| | | | | 203/21 |
| 2016/0221853 | A1* | 8/2016 | Cort | C02F 11/121 |
| 2018/0001291 | A1* | 1/2018 | Nussinovitch | B01J 13/14 |
| 2018/0093247 | A1* | 4/2018 | Longo | B01J 19/2435 |

OTHER PUBLICATIONS

Bayoumi, et al., Bacteriological systems as a new approach for desalination of salty water, Al-Azhar Bull. Sci., vol. 18 No. 2 (Dec. 2007 p. 37-58, (Year: 2007).*

Figler et al., Effects of Nutrient Content and Nitrogen to Phosphorous Ratio on the Growth, Nutrient Removal and Desalination Properties of the Green Alga *Coelastrum morus* on a Laboratory Scale, Energies, 2021, 14, p. 2112, https://doi.org/10.3390/en14082112 (Year: 2021).*

Zafar et al., Biodesalination using halophytic cyanobacterium Phormidium keutzingianum from brackish to the hypersaline water, Chemosphere, 307 (2022) 136082 (available online Aug. 23, 2022) (Year: 2022).* http://www.kramer-schaumsilikate.de/english.html downloaded 2023 (Year: 2023).*

Lynne S. Cairns, et al., Biofilm formation by Bacillus subtilis: new insights into regulatory strategies and assembly mechanisms, Molecular Microbiology (2014) 93(4), 587-598 (Year: 2014).*

Pablo Marin, et al., Reverse flow reactors as sustainable devices for performing exothermic reactions: Applications and engineering aspects, Chemical Engineering & Processing: Process Intensification 135 (2019) 175-189 (Year: 2019).*

Kristina Meier, et al., Quasi-continuous fermentation in a reverse-flow diafiltration bioreactor, Biochemical Engineering Journal 91 (2014) 265-275 (Year: 2014).*

* cited by examiner

BIODESALINATION USING MICROBIAL ATTACHED GROWTH CULTIVATION

FIELD OF THE INVENTION

The present invention relates to performing biodesalination using microbial attached growth cultivation.

BACKGROUND

Freshwater sources are very scarce. About 3% of the total water on Earth is considered a freshwater source that can be used for drinking purposes. Mostly this freshwater source is available in terms of rivers, streams, lakes, and groundwater. Around 97% of Earth's water belongs to oceans and seawater. This water requires approximately 99% removal of total dissolved solids before consumption for drinking or domestic purposes. The population in coastal regions mostly consumes seawater to meet their daily water and cleaning purposes. Water quality can be compromised for all these uses, except cooking, washing, and bathing. Therefore, seawater treatment can be made efficient by opting for other less energy-demand technologies demands. Domestic water consumption involves cooking, washing, bathing, gardening.

The conventional desalination techniques in coastal regions are based on thermal, pressure driven, and electrochemical processes. These technologies include thermal distillation, reverse osmosis, nanofiltration, and ion exchange membranes. The most significant disadvantage of these processes is high energy consumption, resulting in expensive water treatment technology, and the price of water becomes very high at the consumer end. Another disadvantage is that the brine generation from these technologies is very high. In order to achieve 1 L of potable water from seawater, 1.5 L of brine is generated. Therefore, the disposal of brine directly into seawater disturbs the marine ecosystem. If the removal of brine is disposed of directly on the soil, it may deteriorate soil fertility. Brine disposal management is a huge issue with these available technologies. Therefore, there is a need for natural-based desalination technologies using algae and cyanobacteria that can reduce the salt from seawater.

SUMMARY

In accordance with the present invention, there is provided a biological biodesalination process that can remove salt from the seawater using naturally grown algae/cyanobacteria in an attached growth photobioreactor setup.

In the first embodiment of the present disclosure, there is provided a method for biodesalinating seawater, including (A) cultivating a salt-tolerant organism (B) transferring the salt-tolerant organism to support media; (C) allowing attachment of the salt-tolerant organism to the support media; (D) placing the attached salt-tolerant organism in a reactor containing seawater, whereby the amount of salt ions in the seawater is reduced by the salt-tolerant organism.

In one embodiment of the present disclosure, the salt-tolerant organism may include algae or cyanobacteria strains.

In a preferred embodiment of the present disclosure, the salt-tolerant organism is a cyanobacterium.

In the most preferred embodiment of the present disclosure, the cyanobacterium is *Phormidium keutzingianum*.

In one aspect of the present disclosure, the support media may include waste material such as zeolite, rubber, polylactic acid, expanded glass, crushed aggregates, cotton, wool, plastics, and metal.

In another aspect of the present disclosure, the reactor is a photobioreactor can be a batch reactor, a reverse flow reactor, a fluidized bed reactor, a packed/fixed bed reactor, a plug flow reactor, or a continuous flow reactor.

In one aspect of the present disclosure, the salt ions in the seawater include a chloride ion.

In a further aspect of the present disclosure, the concentration of the chloride ion is reduced from seawater in a range of approximately 25 to 35% w/w within 7 days.

In a preferred embodiment of the present disclosure, there is provided a method for biological desalination, including (A) providing a salt-tolerant organism; (B) transferring the organism to support media; (C) placing the attached biological agent in a photobioreactor containing seawater; (D) implementing desalination cycles, each desalination cycle including (i) pushing influent seawater into the photobioreactor utilizing a pump; (ii) mixing the influent seawater with nutrients that are essential for the growth of the salt-tolerant organism; (iii) providing aeration to the salt-tolerant organism (iv) providing a light source; (v) removing salt ions from the seawater by the salt-tolerant organism that is in contact with the seawater; and (vi) producing an effluent depleted in salt ions from the photobioreactor.

In one embodiment, the salt-tolerant organism can include algae or cyanobacteria strains.

In a preferred embodiment, the salt-tolerant organism is a cyanobacterium.

In the most preferred embodiment, the cyanobacterium is *Phormidium keutzingianum*.

In one aspect of the present disclosure, the support media can include waste material such as zeolite, rubber, polylactic acid, expanded glass, crushed aggregates, cotton, wool, plastics, and metal.

In another aspect of the present disclosure, the reactor is a photobioreactor can be a batch reactor, a reverse flow reactor, a fluidized bed reactor, a packed/fixed bed reactor, a plug flow reactor, or a continuous flow reactor.

In one aspect of the present disclosure, the salt ions in the seawater include a chloride ion.

In a further aspect of the present disclosure, the concentration of the chloride ion is reduced from seawater in a range of approximately 25 to 35% w/w within 7 days.

In a preferred aspect of the present disclosure, the concentration of the chloride ion is removed from seawater in a specific hydraulic retention time ranging from approximately 5 to 21 days.

In a most preferred aspect of the present disclosure, the retention time ranges from approximately 7 to 15 days.

In one aspect of the present disclosure, the effluent is discharged from the photobioreactor from an outlet port under gravity.

In one aspect of the present disclosure, the effluent is collected in a separate container.

BRIEF DESCRIPTION OF THE DRAWINGS

The invention can be better understood with reference to the following figures and description. The accompanying drawings are not intended to be drawn to scale. In the drawings, each identical or nearly identical component that is illustrated in various figures is represented by a like numeral. For purposes of clarity, not every component may be labeled in every drawing. Other features and advantages of this invention will become apparent in the following detailed description of preferred aspects of this invention, taken with reference to the accompanying drawings.

DEFINITIONS

Figure 1:
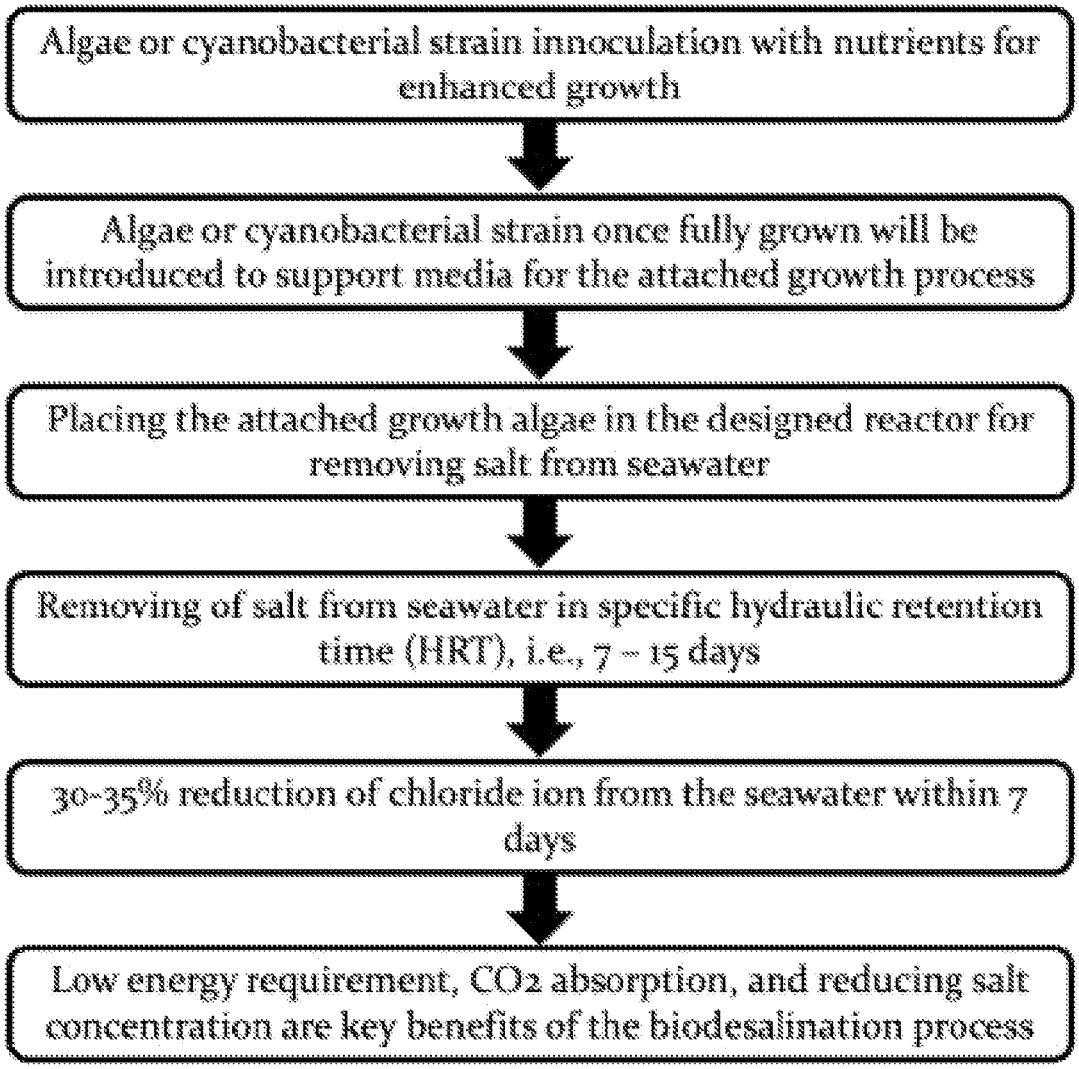
FIG. 1 provides a block diagram for the complete biodesalination process from the beginning.

As used in this description and the accompanying claims, the following terms shall have the meanings indicated, unless the context otherwise requires:

As used in this disclosure, including the appended claims, the singular forms "a," "an," and "the" include plural references, unless the content clearly dictates otherwise, and are used interchangeably with "at least one" and "one or more." Thus, reference to "an aptamer" includes mixtures of aptamers, and the like.

To the extent that the term "include," "have," or the like is used in the description or the claims, such term is intended to be inclusive in a manner similar to the term "comprise" as "comprise" is interpreted when employed as a transitional word in a claim.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

DETAILED DESCRIPTION OF THE DRAWINGS

The present disclosure, in some embodiments, provides cultivating the algae or cyanobacterial strain to grow on support media. The nutrients essential for growth must be available in water so that the growth can be enhanced when these microorganisms get exposed to the salty seawater for the biodesalination process. Certain species have a higher salt tolerating capacity. One such strain is *Phormidium keutzingianum* (*P. keutzingianum*). This strain is a cyanobacterium that can survive in seawater (35-37 g/L of salinity) and increases its growth when seawater is provided with sufficient nutrients. This strain can uptake ions such as chloride ($Cl^-$) which contribute majorly to the salinity and makes seawater bitter. The reduction in the Cl– ions can reduce the amount of salt in the seawater. This cyanobacterium requires the presence of light for the photosynthesis process for its metabolic processes like other eukaryotes and prokaryotes.

In some embodiments, a photobioreactor (PBR) can be designed to receives the light from all possible directions that can cover the maximum surface area. The setup can be installed outdoors with available sunlight hence reducing the energy cost of light in indoor operations that are expensive due to the consumption of using equipment and chemicals. Therefore, this novel attached growth technique has been introduced for the biodesalination process where algae or cyanobacteria can consume salt from the seawater without being detached into the water. The attached growth process is preferred in this innovative solution because algae or cyanobacteria in suspension can be hard to separate from the water. To avoid the algae or cyanobacteria in suspension, attached growth to support media is a useful and novel approach that does not require a separation technique of algae/cyanobacteria from the suspension.

In the first embodiment of the present disclosure, there is provided a method for biodesalinating seawater, including (A) cultivating a salt-tolerant organism (B) transferring the organism to support media; (C) allowing attachment of the organism to the support media; (D) placing the attached biological agent in a reactor containing seawater, whereby the amount of salt ions in the seawater is reduced by the salt-tolerant organism.

In one embodiment of the present disclosure, the salt-tolerant organism can include algae or cyanobacteria strains.

In a preferred embodiment of the present disclosure, the salt-tolerant organism is a cyanobacterium.

In the most preferred embodiment of the present disclosure, the cyanobacterium is *Phormidium keutzingianum*.

In one aspect of the present disclosure, the support media can include waste material such as zeolite, rubber, polylactic acid, expanded glass, crushed aggregates, cotton, wool, plastics, and metal.

In another aspect of the present disclosure, the reactor is a photobioreactor can be a batch reactor, a reverse flow reactor, a fluidized bed reactor, a packed/fixed bed reactor, a plug flow reactor, or a continuous flow reactor.

In one aspect of the present disclosure, the salt ions in the seawater include a chloride ion.

In a further aspect of the present disclosure, the concentration of the chloride ion is reduced from seawater in a range of approximately 25 to 35% w/w within 7 days.

In a preferred embodiment of the present disclosure, there is provided a method for biological desalination, including (A) providing a salt-tolerant organism; (B) transferring the organism to support media; (C) placing the attached biological agent in a photobioreactor containing seawater; (D) implementing desalination cycles, each desalination cycle including: (i) pushing influent seawater into the photobioreactor utilizing a pump; (ii) mixing the influent seawater with nutrients that are essential for the growth of the salt-tolerant organism; (iii) providing aeration to the salt-tolerant organism through an air inlet attached to the photobioreactor; (iv) providing a light source; (v) removing salt ions from the seawater by the salt-tolerant organism that is in contact with the seawater; and (vi) producing an effluent depleted in salt ions from the photobioreactor.

In one embodiment, the salt-tolerant organism can include algae or cyanobacteria strains.

In a preferred embodiment, the salt-tolerant organism is a cyanobacterium.

In a most preferred embodiment, the cyanobacterium is *Phormidium keutzingianum*.

In one aspect of the present disclosure, the support media is any material that can encourage the growth of algae or cyanobacteria, such as waste material such as zeolite, rubber, polylactic acid, expanded glass, crushed aggregates, cotton, wool, plastics, and metal.

In another aspect of the present disclosure, the reactor is a photobioreactor can be a batch reactor, a reverse flow reactor, fluidized bed reactor, packed/fixed bed reactor, plug flow reactor, or a continuous flow reactor.

In one aspect of the present disclosure, the salt ions in the seawater include a chloride ion.

In a further aspect of the present disclosure, the concentration of the chloride ion is reduced from seawater in a range of approximately 25 to 35% w/w within 7 days.

In a preferred aspect of the present disclosure, salt ions are removed from seawater in a specific hydraulic retention time ranging from approximately 5 to 21 days.

In a most preferred aspect of the present disclosure, the retention time ranges from approximately 7 to 15 days.

In one aspect of the present disclosure, the effluent is discharged from the photobioreactor from an outlet port under gravity.

In one aspect of the present disclosure, the effluent is collected in a separate container.

In a preferred aspect of the present invention, the salt-tolerant organism is a photosynthetic organism.

In one aspect of the present invention, the salt-tolerant organism can include, but is not limited to, *Chlorella sorokiniana, Chlorella vulgaris, Chlorococcum* sp., *Desmodesmus communis, Desmodesmus spinosus, Scenedesmus obliquus, Scenedesmus obtusus, Monoraphidium komarkove, Monoraphidium pusillum,* and *Alishewanella* sp. species.

In one aspect of the present disclosure, the photobioreactor is developed from an acrylic plastic pipe that is transparent to allow light to pass through for the photosynthetic process.

In another aspect of the present disclosure, the photobioreactor is developed from at least one of the following light-conducting polymers: polyethylene, polypropylene, polybutylene, polyester, polycarbonate, polyamide, polyvinyl chloride, polyvinylidene chloride, polystyrene, copolymers of butadiene and styrene, polyurethane, polyacrylonitrile, polyacrylate, copolymers, mixed laminations, and combinations thereof of said polymers.

In some aspects of the present disclosure, the photobioreactor (PBR) structure can be vertical or horizontal in orientation. Any shape of PBR can provide more light contact to the algae or cyanobacteria for enhanced growth on support media. The reactor can be designed in a way that can get maximum exposure to sunlight. The influent seawater is mixed with nutrients that are essential for the growth of algae or cyanobacteria. The main objective is to remove the salt from the brackish or seawater. The influent seawater can be treated using the attached growth of algae or cyanobacteria, and the effluent from the PBR can be further treated based on desired water use. The algae and cyanobacteria consume salt for their growth. Reproduction of more cells can uptake the salt from the seawater in a specific hydraulic retention time (HRT). By this technique, the potential to remove salt efficiently can be assured with a minimum detachment of algal or cyanobacterial cells in the effluent.

In some examples, the biodesalination process of the present disclosure involves less energy, and hence there are no excessive greenhouse gas emissions during the operation of this system. It rather requires $CO_2$ for microbial growth, therefore this process can capture $CO_2$ while operating the biodesalination plant of the present invention on a large scale.

In some further examples, the brine from RO plants can be treated with algae and cyanobacteria to produce value-added products. Therefore, a circular economy concept can be developed based on the biodesalination potential of algae and cyanobacteria and the extraction of valuable products.

As a result, the biodesalination process can also deliver a salt reduction of brackish/seawater and valuable market products. Due to low operation costs, the treated water cost using the biodesalination process for the consumer end can also be reduced. The biodesalination process is an environmentally friendly technique with no waste stream and can be enhanced with the amount of salt uptake with more microbial species identification.

In some aspects, the biomass of algae or cyanobacteria attached to support media can be regenerated and reused for further desalination process. Further, the biodesalination process generates less waste as compared to conventional desalination technologies and is less energy-demanding.

In some further aspects, the biomass may be scrapped to extract proteins, lipids, fatty acids, and other biofuels produced by the specific species being cultivated. Such by-products are value-added products that can generate revenue.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these examples while indicating preferred embodiments of the subject technology, are given by way of illustration only. From the above discussion and these Examples, one skilled in the art can ascertain the essential characteristics of the subject technology and without departing from the spirit and scope thereof, can make various changes and modifications of the subject technology to adapt it to different uses and conditions.

Preparation of Algae or Cyanobacteria to Support Media

Algae and cyanobacteria require some essential supplements to grow. *Phormidium keutzingianum* was inoculated in an Erlenmeyer flask and cultivated in BG-11 medium at 23° C. with constant illumination of 2885 lux, and subsequently, the *Phormidium keutzingianum* solution was scaled up to 5,000 mL in a Schott bottle under continuous air supply with agitation at 2,000 rpm.

Figure 2:
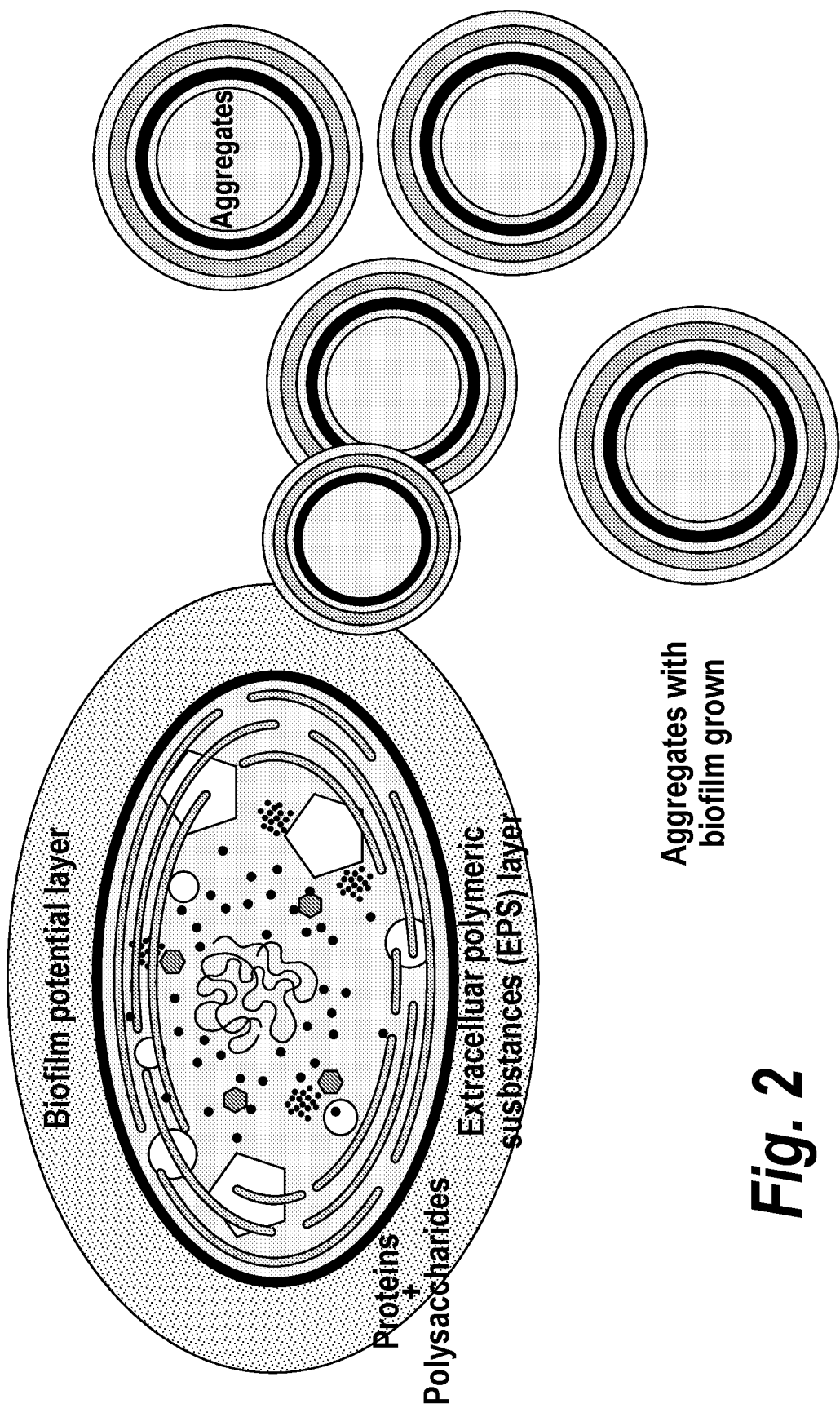
FIG. 2 provides a schematic diagram for the cultivation procedures of algae or cyanobacteria on support media FIG. 3 provides a schematic diagram of the PBR developed for seawater biodesalination.

The fully cultivated bloom of *Phormidium keutzingianum* was introduced to support media where these microorganisms attach to the surface of support media. These microorganisms develop a layer of cells on the surface of support media. The attachment is usually supported by the secretion these microorganisms generate, and these secretions are known as extracellular polymeric substances (EPS). Due to available nutrients, these EPS are generated in larger quantities, and hence the support media is covered by the biofilms on the support media. Therefore, the algae or cyanobacteria can attach to a surface where they continuously develop biofilms. A schematic diagram is shown in FIG. 2 for the process of attached growth to support media.

The optimal amounts of reagents, nutrient media, and algae or cyanobacteria treatment methods for a particular aspect used in the photobioreactor of the present invention can be readily determined by those skilled in the art having the teachings herein.

Development and Configuration of a Photobioreactor (PBR)

Figure 3:
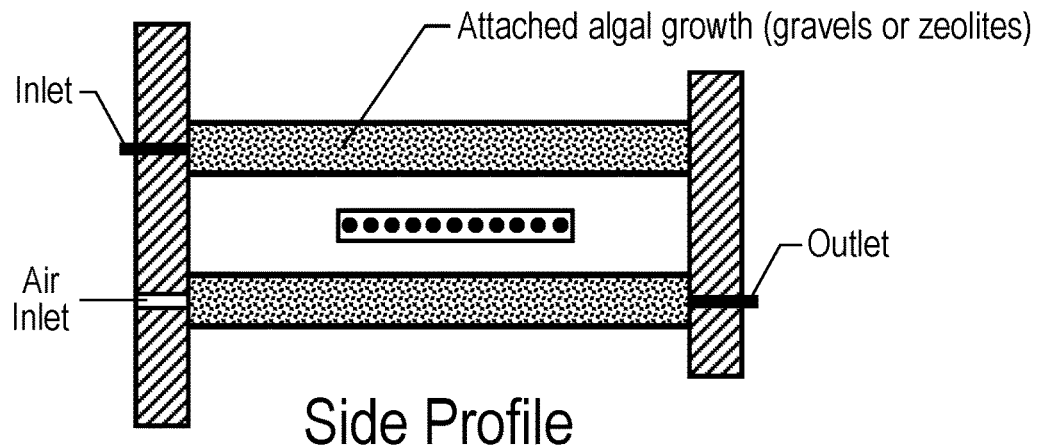
Figure 3:
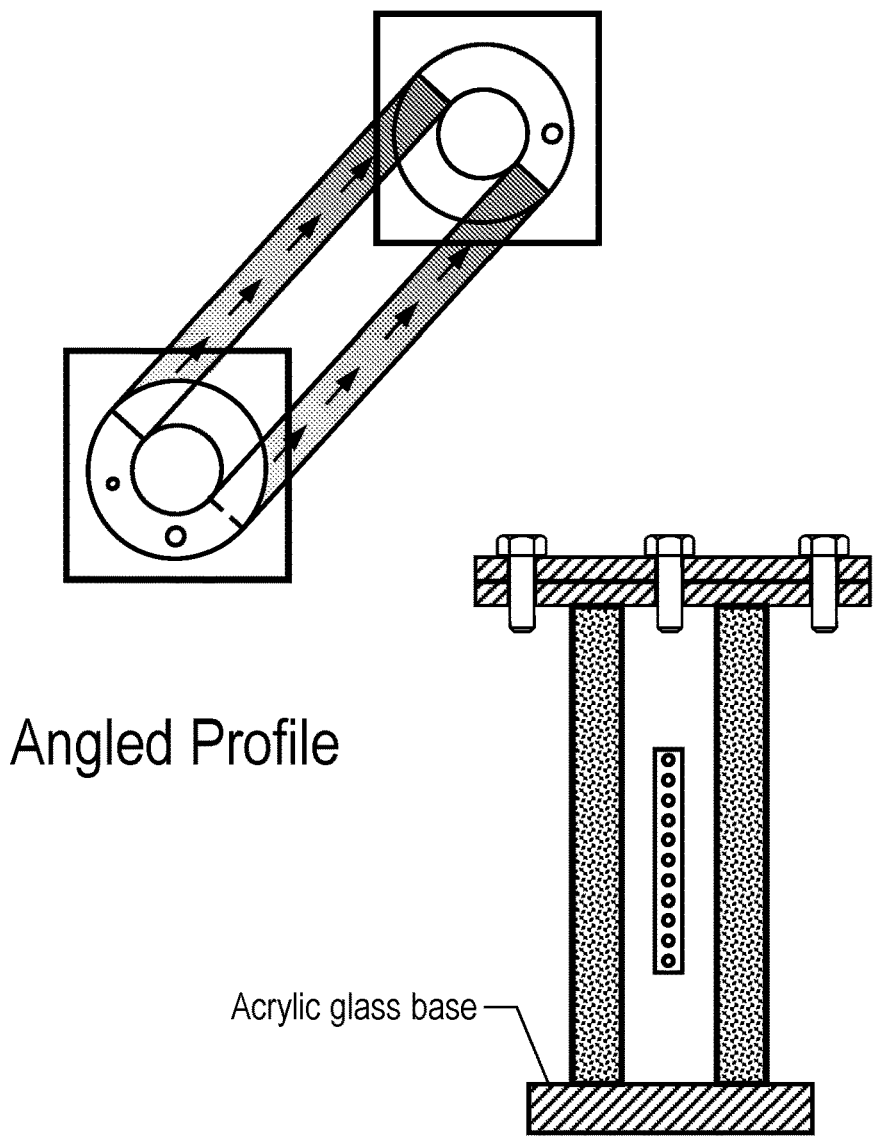
Figure 4:
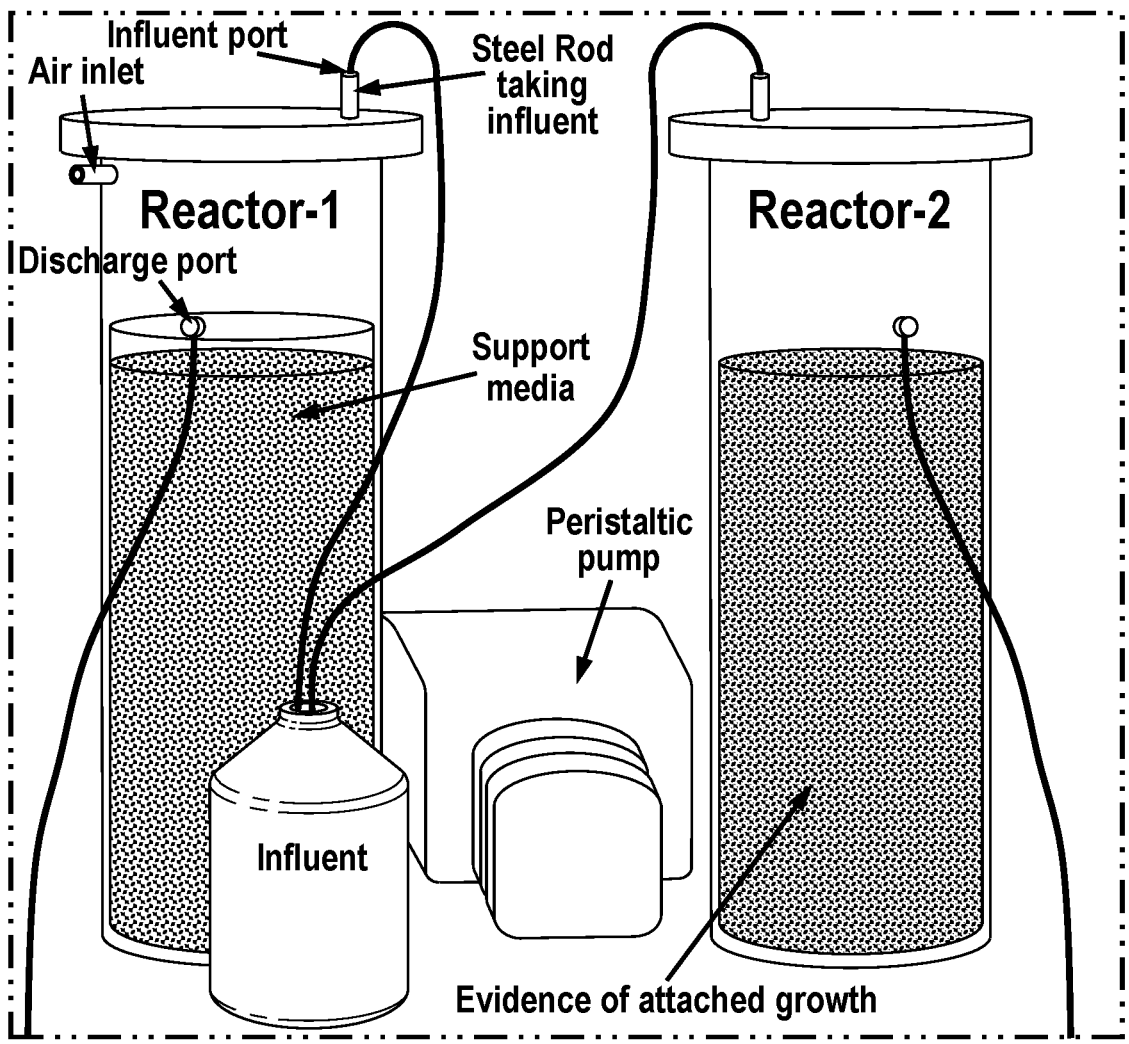
FIG. 4 provides an experimental setup of the biodesalination process.

A photobioreactor (PBR) is developed from an acrylic plastic pipe that is transparent in color to allow sunlight to pass for the photosynthesis process. The outer pipe diameter is 15 cm, and the inner diameter of the pipe is 7 cm. The working space where the support media can be added in the PBR is 8 cm. The PBR setup is kept hollow from the middle part so that maximum light can pass through the reactor. Support media in the central region needs light for algae or cyanobacteria to attach to the surface. The length of the PBR is approximately 53 cm. The top of the reactor is sealed with a removable transparent lid of the same material as the PBR. The cover is removable to allow adding or removing support media from the reactor. The inlet port is introduced on the top of the cover, which is connected to a pipe towards the base of the PBR. A vertical reverse flow system is used for the current PBR setup so that the minimum energy can be consumed while operating the device. Influent seawater is pushed into the PBR with the support of a peristaltic pump operating at different revolutions for the set flow rates. The influent seawater completes its hydraulic retention time (HRT) based on flow rate and discharges from the discharge port/outlet port of PBR under gravity. The effluent from the reactor is collected in a separate container. An air connection is provided in the reactor for aeration of the cyanobacteria or algae at 3 mL/min, in which atmospheric $CO_2$ present is essential for the growth of cells. FIG. 3 displays a schematic layout of the PBR. FIG. 4 shows the two PBR setups with different experimental conditions. One PBR is uncovered, i.e., without clothing to maximize the light intensity, and is called Reactor 1. The other one is named Reactor 2, which is covered with clothing for reduced light intensity.

Performance Evaluation of Biodesalination Process

The biodesalination performance is evaluated on the chloride ion removal, which is presented in the form of C/Co. Co is the seawater's initial chloride concentration (mg/L), and C is the measured chloride ion concentration at time (mg/L). The concentration of chloride ions is measured using the United States Environmental Protection Agency (U.S. EPA) standard method. This method provides that the chloride ion concentration can be measured by Ion Chromatography (IC). Therefore, all the reported C/Co chloride ion concentrations are reported from IC. Another performance indicator is the change of color in the effluent (treated seawater), which according to this setup, should be minimum. This setup was invented to avoid maximum cell detachment, where the attachment of algae or cyanobacteria should be reduced in the effluent. For this reason, optical density (OD) at 620 nm wavelength was measured regularly to monitor the performance of cell detachment. Usually, there is an exponential increase in the OD values in suspended growth studies.

EXAMPLES

The disclosure will be more fully understood upon consideration of the following non-limiting Examples. It should be understood that these examples, while indicating preferred embodiments of the subject technology, are given by way of illustration only. From the above discussion and these Examples, one skilled in the art can ascertain the essential characteristics of the subject technology and without departing from the spirit and scope thereof, can make various changes and modifications of the subject technology to adapt it to various uses and conditions. As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Example 1—Removal of Chloride Ion in Biodesalination Attached Growth Setup

Figure 5:
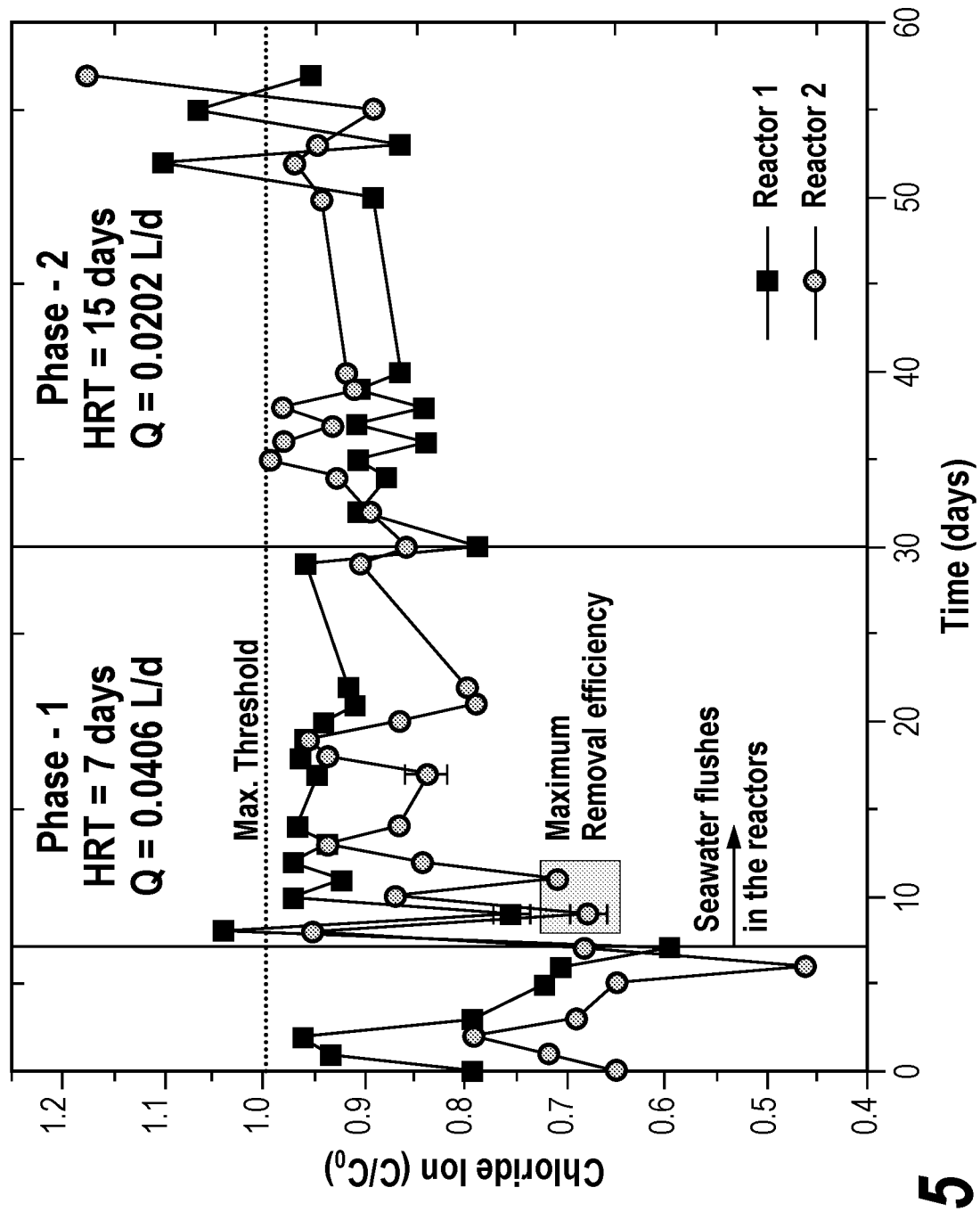
FIG. 5 provides chloride ion removal for CFR biodesalination setup in attached growth setup for Reactors 1 and 2.

The removal of chloride ions using a continuous flow reactor (CFR) based on attached growth algae or cyanobacteria is shown in FIG. 5. The two phases have been subdivided in FIG. 5, based on different HRT and flow rates. The chloride ion removal has occurred in both reactors and in both phases. On the $9^{th}$ day of the experiment, the maximum chloride ion removal of 32% is observed for Reactor 2, followed by the $11^{th}$ day, which is around 30%. For Reactor 1 in phase-1, 25% of chloride ion removal is observed on the $9^{th}$ day. Phase-1 has shown maximum chloride ion removal for Reactor 2.

Reactor 1 has responded to a slower chloride ion removal which could be due to many other factors, including increased light intensity; more sunlight may have raised the temperature of the water, which slows down the growth of algae and cyanobacteria. However, both reactors have shown significant chloride ion removal without any modification in their metabolism. The same support media is used in these experiments with similar characteristics and the same conditions other than light intensity. By the end of the experiment, the chloride ion uptake had been reduced in both reactors. For Reactor 1, the removal efficiency of chloride ion has reduced to 5%, while for Reactor 2, the chloride ion removal is zero. Similarly, for phase-2, Reactor 1 dominated with a maximum removal efficiency of 20%. The CFR reactor type can be a limiting factor compared to batch reactors only for the case of algae and cyanobacteria due to several factors. In CFR, the hydraulic retention time is provided for seven days in phase-1 for both reactors 1 & 2. In phase-2, the HRT is increased to 15 days, which means the calculated flow rate is further reduced, passing through the support media. The conditions were different in both phases as there is a time shift and weather conditions also changed during the experimentations. The temperature during phase-2 increased by ±10·C in comparison to phase-1, which could be a limiting factor. The slower flow rates might have increased the evaporation during the experiment conducted. However, there is still a reduction in chloride ion concentration during phase-2, which is insignificant compared to phase-1.

Effect of Cell Detachment Based on Optical Density Measurements

The cell detachment can be estimated by measuring the optical density parameter. The optical density is a measure to evaluate the turbidity effect in water or the growth change of suspended particles (algae or cyanobacteria) in water. The studies conducted on algae and cyanobacteria, which measured the optical density, usually measure the increase in the number of cells.

In this experiment, we measured the optical density to estimate the efficiency of the attached growth system. The number of cells increases the chlorophyll concentration at different wavelengths, i.e., 620, 680, 720, and 750 nm, which determines the growth of that particular algae or cyanobacterium. Therefore, the effluent was collected from both reactors and measured for OD to check the cell detachment rate. The lesser OD values indicate that in the effluent, there were fewer detached cells and less absorption for chlorophyll or any other pigment generated by these microorganisms.

Figure 6:
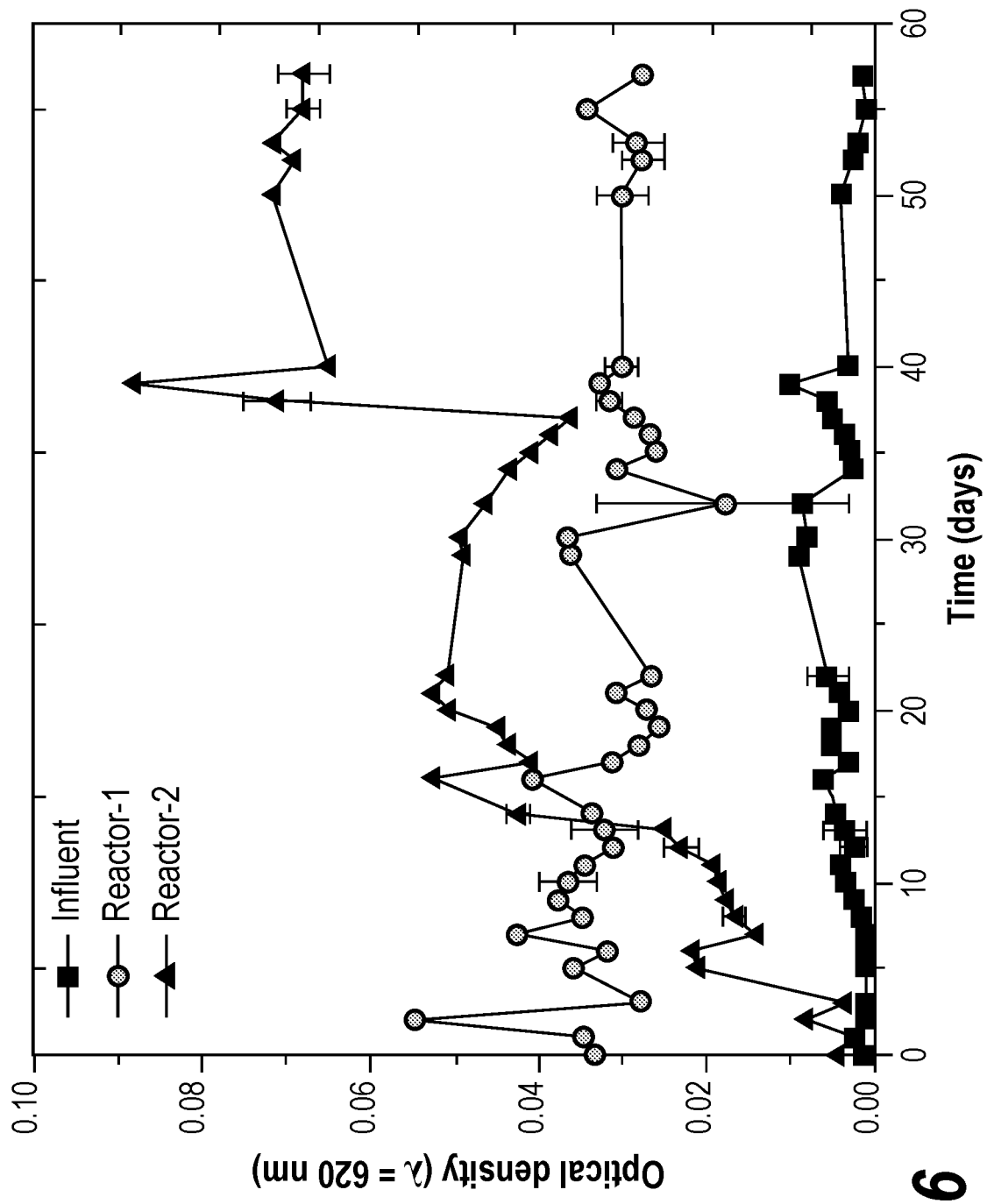
FIG. 6 provides an optical density parameter as a function of the cell detachment rate.

FIG. 6 displays the OD curves for influent, Reactor 1, and Reactor 2. Influent is consistently lower between the OD values of 0.001 to 0.003, which should not have any algae or cyanobacterial growth, and is shown in the results. For Reactor 1, the OD values fluctuate between 0.03 to 0.04, which is also a positive sign that Reactor 1 has not detached more cells while the experiment was running. For Reactor 2, the cell detachment is reported higher in comparison to Reactor 1. The highest OD value of 0.09 is observed on the $39^{th}$ day of the experiment. This indicates that in Reactor 2, the cell detachment rate is higher in comparison to Reactor 1. It is also observed in Reactor 2 that the growth of cells in the effluent is consistently increasing with time.

Effect of pH During the Experimental Setup

Figure 7:
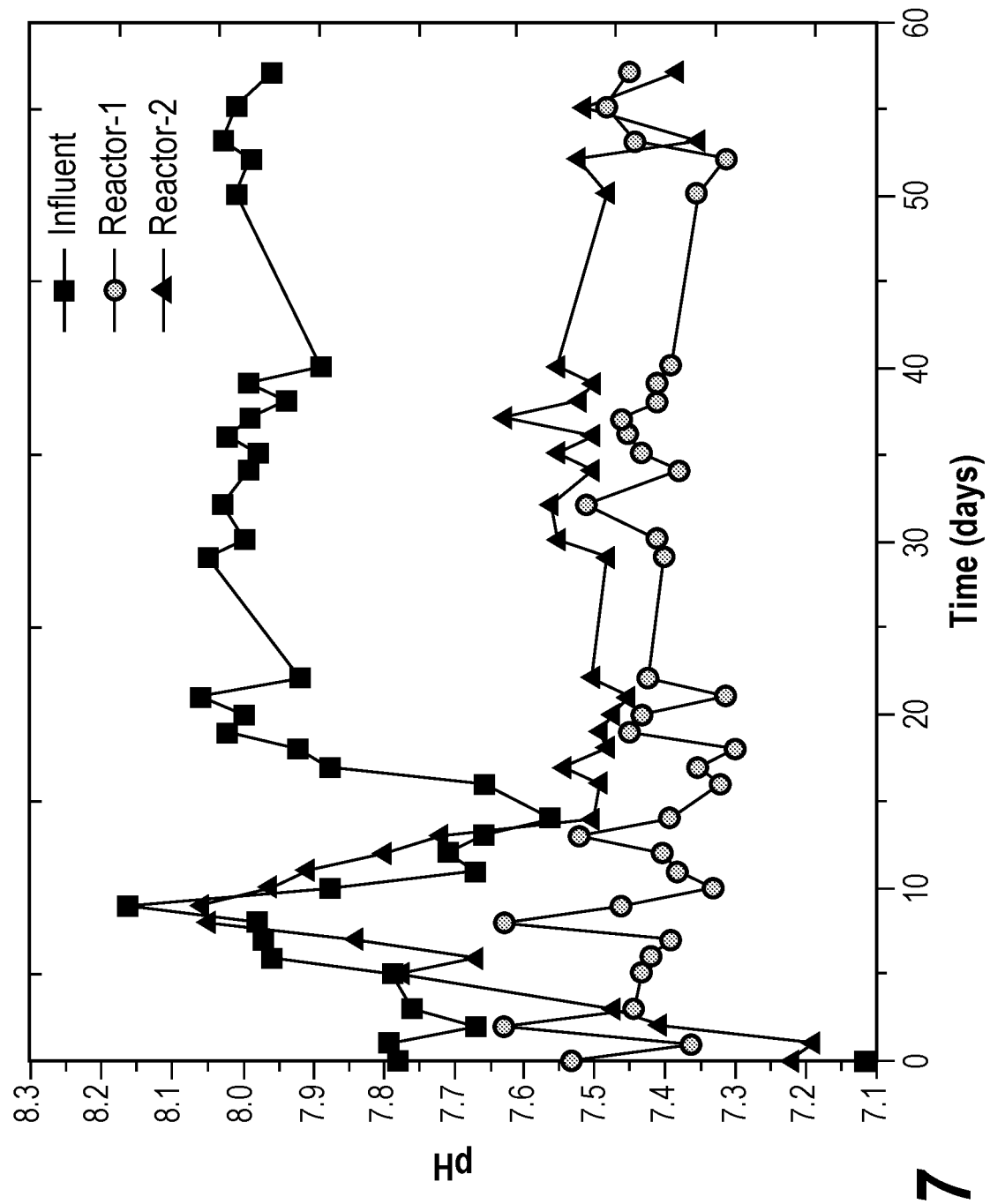
FIG. 7 provides pH variations during the biodesalination process in the attached growth process.
Figure 8:
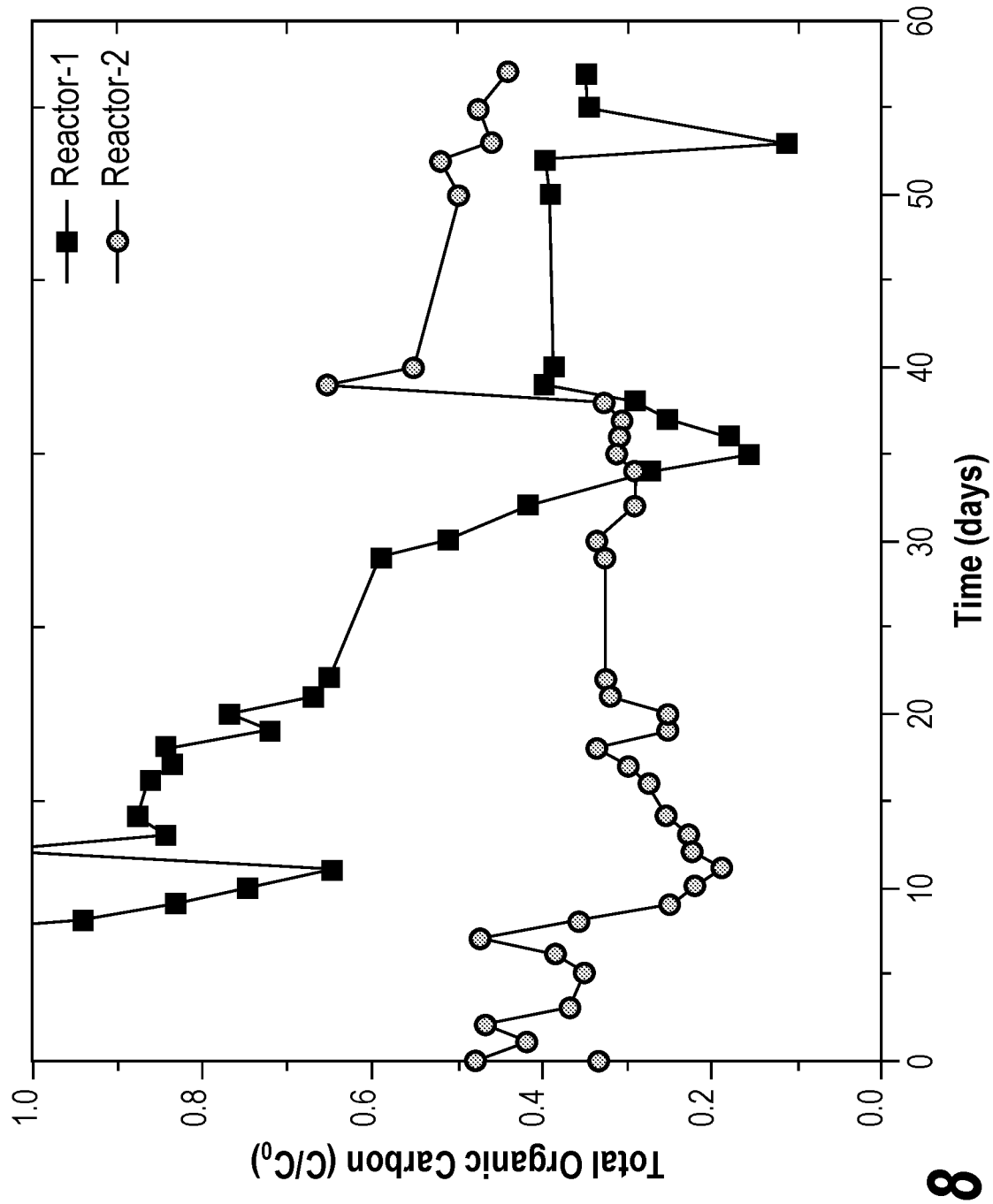
FIG. 8 provides the total organic carbon (C/CO) removal efficiency in reactors 1 and 2 during the experiment.

The pH variations are consistent throughout the experiment. FIG. 7 displays the pH during the experimentation for the influent, Reactor 1, and Reactor 2. The pH of influent seawater was consistent between the range of 7.90 to 8.10. For Reactor 1, the pH values fluctuate between the range of 7.3 to 7.5. The pH values for Reactor 1 have shown consistency as the values were not significantly different from each other. The pH in reactor 1 could be consistent because of active aeration that kept the pH on the scale between 7.3 and 7.5. However, the attached growth in Reactor 1 has shown a little delay compared to Reactor 2. Reactor 2, on the other hand, has shown more variations due to the high growth activity. The most elevated pH of 8.05 was observed on the 10th day of the experiment. And with the experiment continued, a decline in pH was observed. The lowest pH of 7.35 is achieved on the $53^{rd}$ day of the experiment. The algae and cyanobacteria can grow better if the pH of water is toward the alkaline scale. And it has been reported in the literature that the carbon fixation cycle in algae and cyanobacteria can increase the pH. However, since we are continuously aerating the reactors, this regulates the lowering of pH and maintaining normal pH ranges in both reactors. However, the increase in OD and high pH values for Reactor 2 justifies some reasoning for more cell growth in suspension, and high pH values are correlated.

Effect of Total Organic Carbon Reduction

The total organic carbon is a good parameter to estimate water quality. The parameter estimates the amount of dissolved organic carbon available in the water sample. Therefore, the samples from both reactors are assessed throughout the treatment cycle. The TOC cycle in reactor 1 begins with a delay of 8 days.

However, on the $10^{th}$ day, the TOC removal of 38% is observed in reactor 1. Similarly, reactor 1 displays the highest removal efficiency on days 35 and 53, with corresponding removal efficiencies of around 85% and 90%, respectively. The higher removal efficiencies are observed during phase-2 in Reactor 1. On the contrary, Reactor 2 has shown high removal efficiency of 80% approx. On the $10^{th}$ day of the experiment. Reactor 2 performed much better during phase-1. In phase-2, for Reactor 2, the removal efficiency was reduced with time. One reason could be that the reduction in chloride ion removal might affect TOC. Or the cell regrowth phase might have occurred in Reactor 2. The complete treatment cycle corresponds to that in both reactors, TOC reduction is accomplished with good removal efficiencies. More than 60% removal is obtained in Reactor 1 through the treatment. Similarly, in Reactor 2, more than 80% of TOC removal is achieved during phase-1. TOC removal can also predict that the availability of organic carbon reduced with time, which indicates that microbial activity continued in the reactors that have consumed the dissolved organic carbon from the reactors. Therefore, biodesalination with an attached growth process can remove salt from the seawater as well as the process can reduce the organic carbon content from the seawater. This system can be upgraded into the pilot-scale mode for operation at some municipality scale to at least be used in gardening and some basic industrial needs. The RO load will be reduced, and less energy consumption will reduce the cost of water use. The process is still at the beginning stages of the investigation, which can be developed further with the passage of time and more advancements in the system design.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

What is claimed is:

1. A method for biodesalinating seawater, comprising: (A) cultivating a salt-tolerant algae or cyanobacteria strain; (B) transferring the salt-tolerant algae or cyanobacteria strain to a solid support media; (C) allowing attachment of the salt-tolerant algae or cyanobacteria strain to the support media; (D) placing the attached salt-tolerant algae or cyanobacteria strain in a light transparent vertical reverse flow photobioreactor containing seawater, whereby the amount of salt ions in the seawater is reduced by the salt-tolerant algae or cyanobacteria strain.

2. The method of claim 1, wherein the salt-tolerant algae or cyanobacteria strain is a cyanobacterium.

3. The method of claim 2, wherein the cyanobacterium is *Phormidium keutzingianum*.

4. The method of claim 1, wherein the solid support media is selected from the group consisting of waste material selected from the group consisting of zeolite, rubber, polylactic acid, expanded glass, crushed aggregates, cotton, wool, plastics, and metal.

5. The method of claim 1, wherein the salt ions in the seawater comprise a chloride ion.

6. The method of claim 5, wherein the concentration of the chloride ion is reduced from seawater in a range of approximately 25 to 35% w/w within 7 days.

7. The method of claim 1, wherein the desalination process is carried out in the presence of at least one light source and nutrients that are essential for the growth of the salt-tolerant algae or cyanobacteria strain.

8. A method for biological desalination, comprising: (A) providing a salt-tolerant algae or cyanobacteria strain; (B) transferring the salt-tolerant algae or cyanobacteria strain to a solid support; (C) placing the attached salt-tolerant algae or cyanobacteria strain in a light transparent vertical reverse flow photobioreactor containing seawater; (D) implementing desalination cycles, each desalination cycle comprising:

(i) pushing influent seawater into the photobioreactor utilizing a pump; (ii) mixing the influent seawater with nutrients that are essential for the growth of the salt-tolerant algae or cyanobacteria strain; (iii) providing aeration to the salt-tolerant algae or cyanobacteria strain; (iv) providing a light source; (v) removing salt ions from the seawater by the salt-tolerant algae or cyanobacteria strain that is in contact with the seawater; (vi) producing an effluent depleted in salt ions from the photobioreactor.

9. The method of claim 8, wherein the salt-tolerant algae or cyanobacteria strain is a cyanobacterium.

10. The method of claim 9, wherein the cyanobacterium is *Phormidium keutzingianum*.

11. The method of claim 8, wherein the support media is selected from the group consisting of waste material selected from the group consisting of zeolite, rubber, polylactic acid, expanded glass, crushed aggregates, cotton, wool, plastics, and metal.

12. The method of claim 8, wherein the salt ions in the seawater comprise a chloride ion.

13. The method of claim 12, wherein the removal of chloride ion from the seawater is approximately from 25 to 35% w/w within 7 days.

14. The method of claim 8, wherein salt ions are removed from seawater in a specific hydraulic retention time ranging from approximately 5 to 21 days.

15. The method of claim 13, wherein the retention time ranges from approximately 7 to 15 days.

16. The method of claim 8, wherein the effluent is discharged from the photobioreactor from an outlet port under gravity.

17. The method of claim 1, wherein the light transparent vertical reverse flow photobioreactor is developed from a light-conducting polymer selected from the group consisting of at least one of the following light-conducting polymers: polyethylene, polypropylene, polybutylene, polyester, polycarbonate, polyamide, polyvinyl chloride, polyvinylidene chloride, polystyrene, copolymers of butadiene and styrene, polyurethane, polyacrylonitrile, polyacrylate, copolymers, mixed laminations, and combinations thereof of said polymers.

18. The method of claim 8, wherein the light transparent vertical reverse flow photobioreactor is developed from a light-conducting polymer selected from the group consisting of at least one of the following light-conducting polymers: polyethylene, polypropylene, polybutylene, polyester, polycarbonate, polyamide, polyvinyl chloride, polyvinylidene chloride, polystyrene, copolymers of butadiene and styrene, polyurethane, polyacrylonitrile, polyacrylate, copolymers, mixed laminations, and combinations thereof of said polymers.

* * * * *